United States Patent [19]

Seaber et al.

[11] E Patent Number: Re. 32,513

[45] Reissued Date of Patent: Oct. 6, 1987

[54] METHOD FOR DISPENSING AT A VISIBLY DETECTABLE RATE, CONTINUOUSLY OR DISCONTINUOUSLY, FOR DISCRETE PERIODS OF TIME AT A STEADY RATE, A VOLATILE COMPOSITION OF MATTER FROM A CONTAINER INTO THE ATMOSPHERE AS WELL AS THE CONTAINER USED IN THE METHOD

[75] Inventors: Geoffrey B. Seaber, Ijsselstein, Netherlands; Augustinus G. van Loveren, Ryebrook; Marina A. Munteanu, New York, both of N.Y.

[73] Assignee: International Flavors & Fragrances Inc., New York, N.Y.

[21] Appl. No.: 842,486

[22] Filed: Mar. 21, 1986

Related U.S. Patent Documents

Reissue of:

[64] Patent No.: 4,387,849
Issued: Jun. 14, 1983
Appl. No.: 245,542
Filed: Mar. 19, 1981

U.S. Applications:

[63] Continuation of Ser. No. 620,239, Jun. 13, 1984, abandoned.

[51] Int. Cl.[4] ..... A61L 9/04; A61L 9/01; A61L 9/12

[52] U.S. Cl. ..... 239/6; 239/34; 239/54; 239/56; 239/60

[58] Field of Search ..... 239/6, 34, 53, 55, 56, 239/60, 54

[56] References Cited

U.S. PATENT DOCUMENTS

| | | | |
|---|---|---|---|
| 3,770,199 | 11/1973 | Hoek et al. | 239/54 |
| 4,063,383 | 12/1977 | Green | 47/1.1 |
| 4,145,001 | 3/1979 | Weyenberg et al. | 239/56 |
| 4,158,440 | 6/1979 | Sullivan et al. | 239/56 X |
| 4,161,283 | 7/1979 | Hyman | 239/55 |
| 4,277,024 | 7/1981 | Spector | 239/56 X |

FOREIGN PATENT DOCUMENTS

| | | |
|---|---|---|
| 52650 | 8/1977 | Israel . |
| 55-78965 | 6/1980 | Japan . |
| 55-81655 | 6/1980 | Japan . |
| 55-36515 | 9/1980 | Japan . |
| 8020178 | 5/1980 | Netherlands . |
| WO81/00051 | 1/1981 | PCT Int'l Appl. . |

*Primary Examiner*—Jeffrey V. Nase
*Attorney, Agent, or Firm*—Arthur L. Liberman

[57] ABSTRACT

Described is a hollow container comprising a shell which is at least partially porous, containing an entrapped volatile substance and a process for dispensing the volatile substance at a visibly detectable rate, continuously or discontinuously, for discrete periods of time at a steady state, the volatile composition being in the alternative, a perfume composition, a deodorant composition, an air freshener composition, an insecticide composition, a herbicide composition, an odor masking composition, a pheremone composition, an animal repellent composition, or an insect repellent composition. The said container containing the entrapped volatile substance ceases to operate, discretely, when said container is placed in an outer air-tight container. The structure consisting of the outer container and the inner container is also a part of our invention.

5 Claims, 22 Drawing Figures

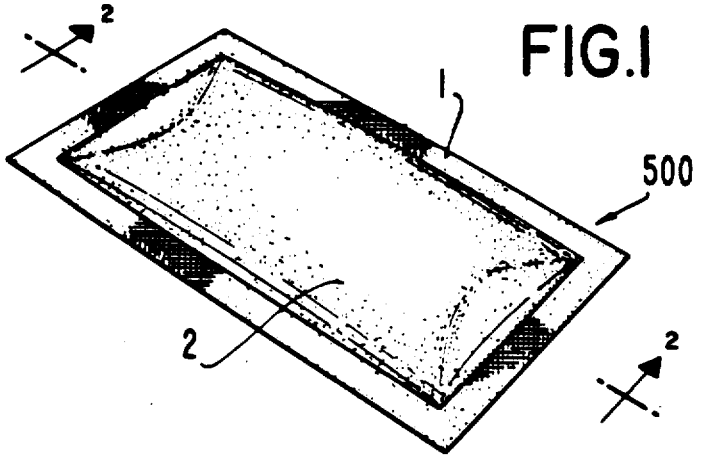
FIG.1
FIG.2
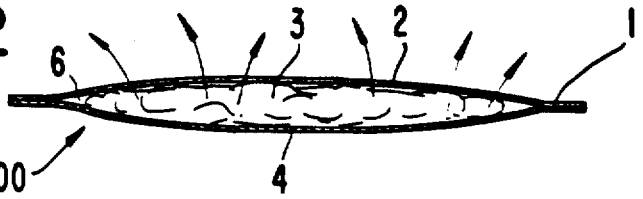
FIG.3
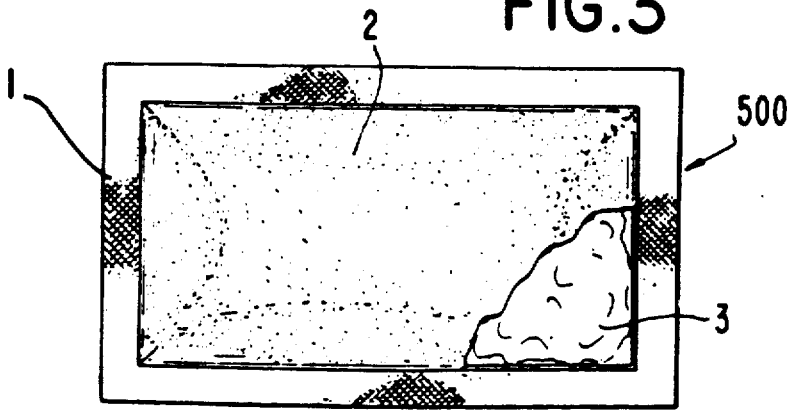

FIG.4
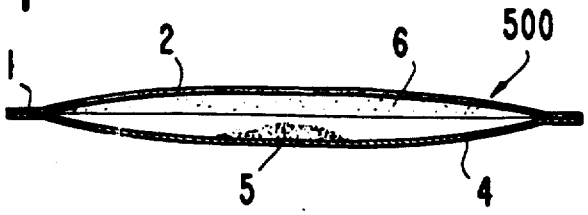
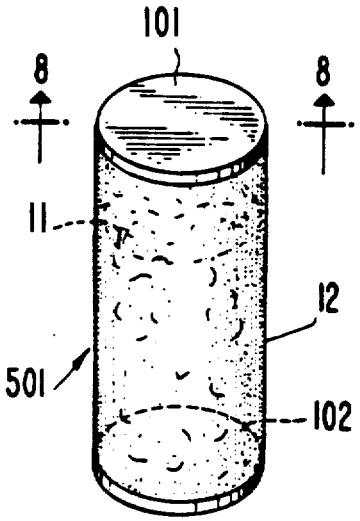
FIG.5
FIG.7
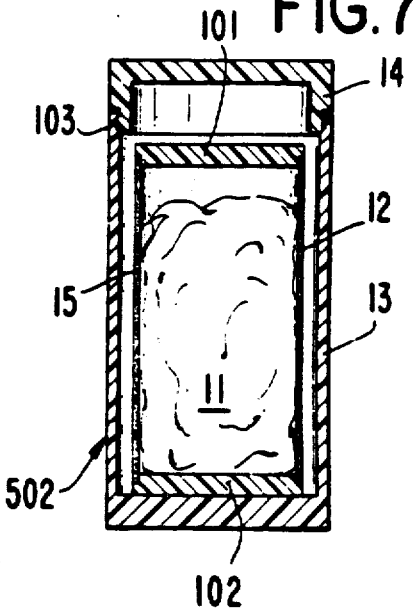
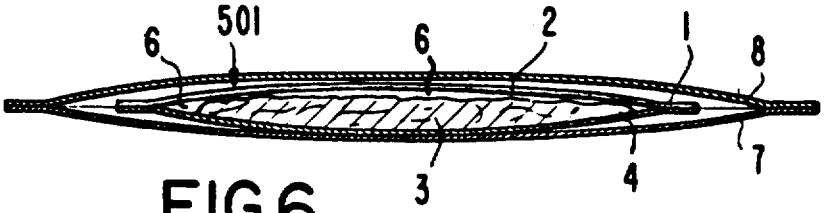
FIG.6

FIG.8
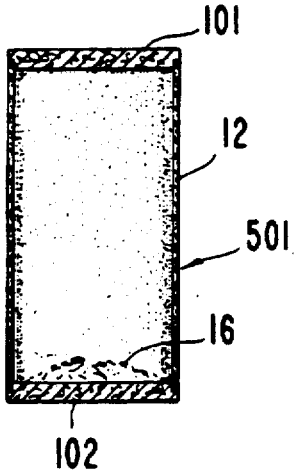
FIG.9
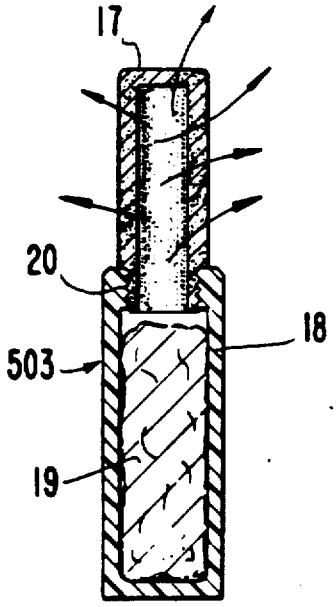
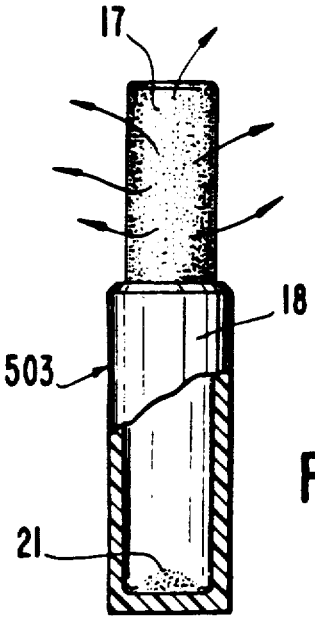
FIG.10

FIG.11
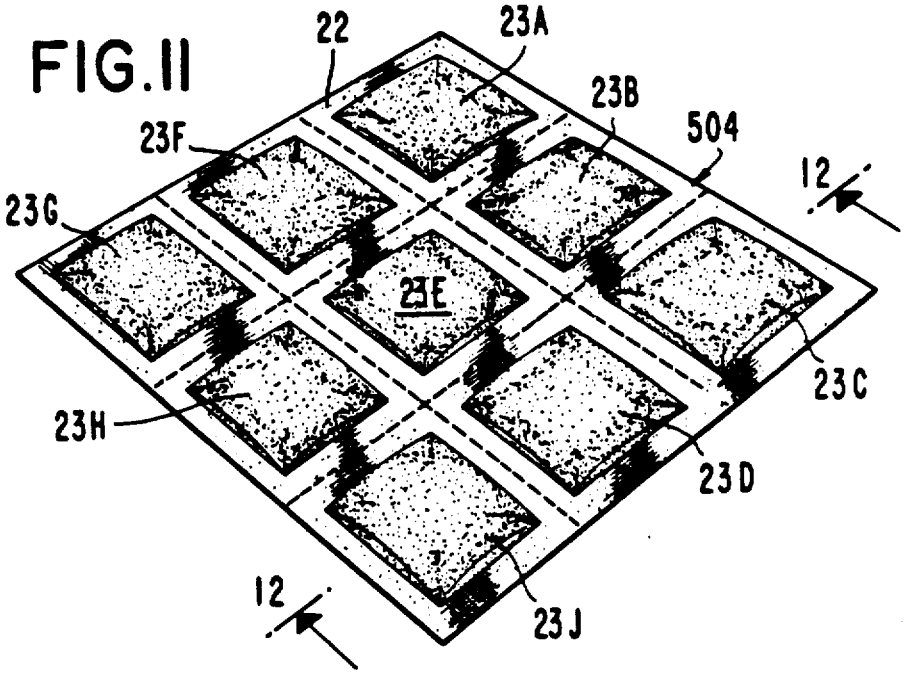
FIG.12
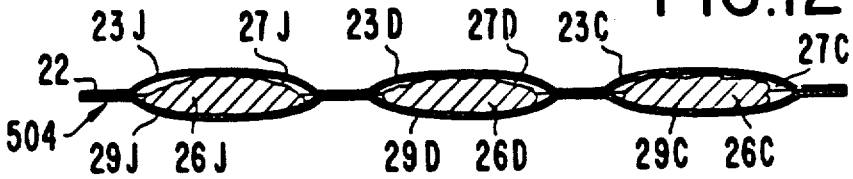
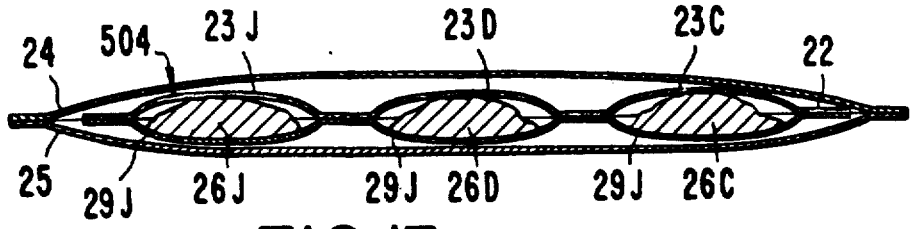
FIG.13

FIG.14
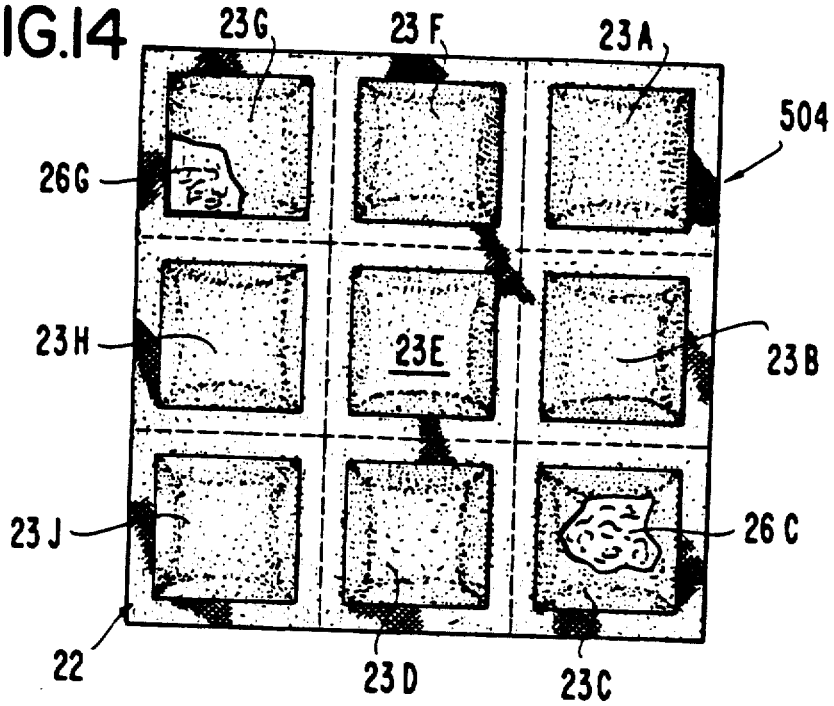
FIG.15
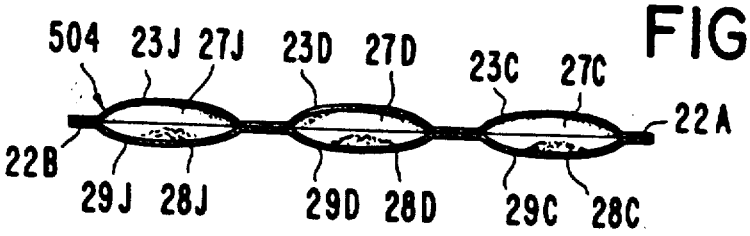
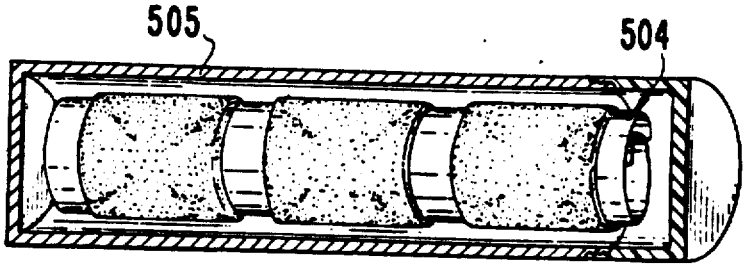
FIG.16

FIG.17
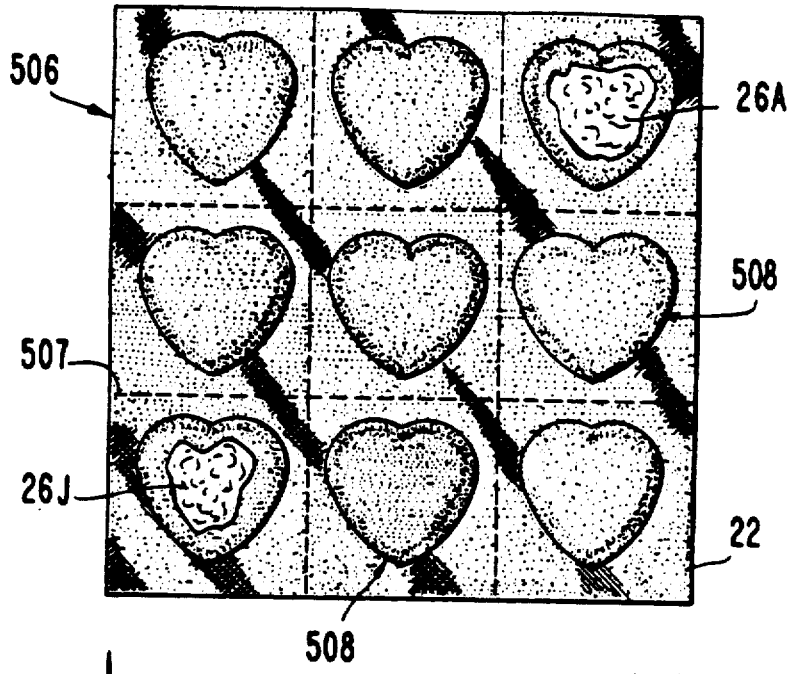
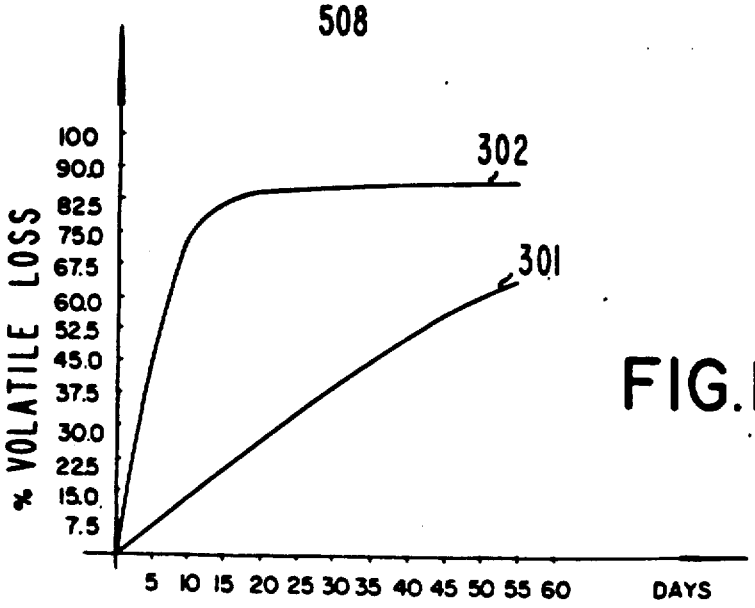
FIG.19

FIG.20
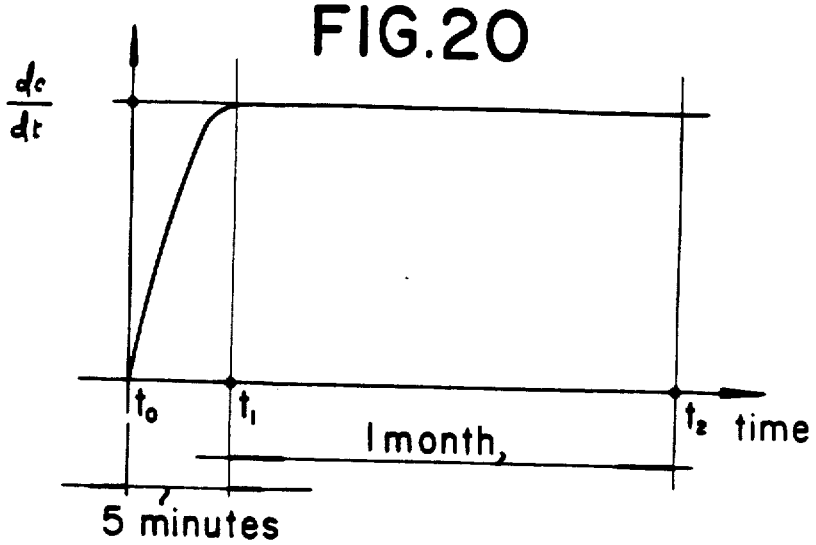
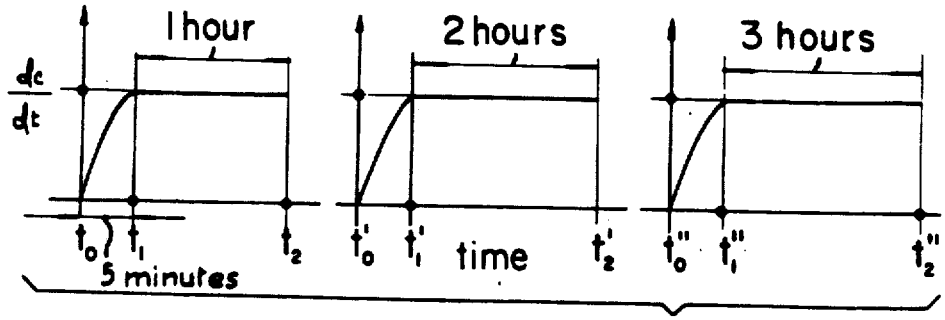
FIG.21
FIG.22
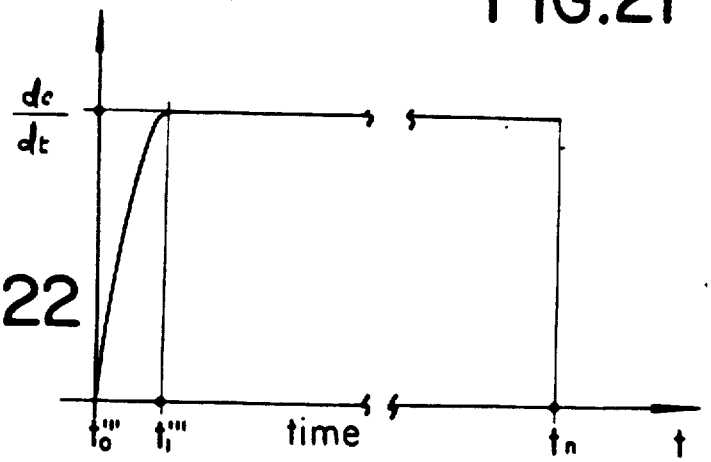

METHOD FOR DISPENSING AT A VISIBLY DETECTABLE RATE, CONTINUOUSLY OR DISCONTINUOUSLY, FOR DISCRETE PERIODS OF TIME AT A STEADY RATE, A VOLATILE COMPOSITION OF MATTER FROM A CONTAINER INTO THE ATMOSPHERE AS WELL AS THE CONTAINER USED IN THE METHOD

Matter enclosed in heavy brackets [ ] appears in the original patent but forms no part of this reissue specification; matter printed in italics indicates the additions made by reissue.

*This is a continuation, of application Ser. No. 620,239, filed 6/13/84, now abandoned, which, in turn, is a reissue application of U.S. Letters Patent, Ser. No. 245,542 filed on 3/19/81, now U.S. Pat. No. 4,387,849 issued June 14, 1983.*

BACKGROUND OF THE INVENTION

Our invention provides volatile substance-emitting apparatus and methods for producing same and for using same wherein the volatile substance can be an air freshener, standard aromatizing material, odor maskants, insecticides, insect repellants, animal repellants, herbicies, pheremones and the like. These volatile substances have previously been used with the following delivery systems:

aerosols;
gels;
paper;
felt;
large pore polymers;
powders;
candles; and
wick-containing liquids.

With the exception of aerosols, the concentration and rate of release of volatile substance, e.g., perfume, into the atmosphere surrounding the container or emitting apparatus has been a function of the rate of evaporation of volatile material which, in turn, has been a function of the remaining concentration of volatile material in the container or emitting apparatus. Accordingly, the rate of mass transfer (e.g., diffusion in certain instances) of the volatile substance into the surrounding atmosphere has, in the prior art, been "first order", that is, a function of the concentration previously present, e.g.:

$$\frac{dc}{dt} = kc$$

Furthermore, with respect to the apparatus of the prior art there has been no practical way for ascertainment by the user as to whether or not the bulk of the volatile material has been depleted at a particular point in time. In all instances it is impossible to determine precisely when the volatile substance is no longer being discharged in an effective quantity and/or concentration per unit time into the atmosphere surrounding the container. In those situations where an aroma is being emitted, the actual aroma is usually relatively powerful during the emission notwithstanding the rate of emission of active agent and said aroma retains its power even after its practical effect (e.g., air freshening) is deminimis.

Thus, in Japanese Pat. No. J8-0036,515 assigned to Akane Soji K K, printings from which fragrance is gradually emitted are indicated to be produced by a process comprising (1) preparing fragrance-emitting ink compositions by dispersing (a) fragrance-emitting bases prepared by mixing perfume solutions with thermoplastic resins at elevated temperatures to homogenize the mixture, followed by cooling the mixture to separate fine particles of gelled resin in which the perfume is occluded in (b) a solution of film-forming material and (2) printing the base material with this fragrance-emitting ink composition.

Scent-releasing polyurethane foams are shown to be prepared in German published Application No. 2,945,757 (assigned to the Tenneco Chemical, Inc.). In published Application No. 2,945,757, it is indicated that a polyurethane foam containing a particulate filler and perfume is prepared by first mixing the filler with the perfume and adding this mixture to a liquid polyol and finally mixing the thus-obtained composition with an organic polyisocyanate, water and a catalyst to produce the resulting foam. It is indicated that the resulting material is used as an air freshener, deodorant, perfume sachet and the like. It is further indicated that the foam releases the perfume at a limited and constant rate. The said published German Application corresponds to U.S. Pat. No. 4,226,944 issued on Oct. 7, 1980.

U.S. Pat. No. 4,247,498 issued on Jan. 27, 1981 discloses a method for preparing a homogeneous microporous cellular polymer structure which evolves perfumes, insect repellants, odor masking agents and the like at a slow and steady rate. The process of U.S. Pat. No. 4,247,498 comprises (i) heating a mixture of a polymer which may be an olefinic polymer, condensation polymer, oxidation polymer or a blend thereof and a "compatible liquid" to a temperature and for a time sufficient to form a homogeneous solution, (ii) forming at substantially the same time a plurality of liquid droplets of substantially the same size in a continuous liquid polymer phase by cooling the solution, (iii) continuing cooling to solidify the polymer, (iv) then at least partially displating the "compatible liquid" with a perfume, an odor masking agent, an insect repellant or the like. It is indicated at column 15, line 30 of U.S. Pat. No. 4,247,498 that the disclosed system may be used to create a "thin film of about 1 mil or less up to a relatively thick block of thickness of about 2½ inches".

Japanese published Application No. J5-5081,655 assigned to Kureha Chemical Industries KK discloses a slow release air aromatizing composition which comprises an aqueous solution of water soluble high molecular weight substance of viscosity 500–30,000 cps such as polyvinyl acetate, carboxymethyl cellulose, sodium alginate, xanthan gum, etc. admixed with an oil soluble perfume or a water soluble perfume.

Nothing in the prior art, however, discloses the novel structure and process for preparing same of our invention wherein a commercially viable structure capable of dispensing at a steady state, at a visibly detectable rate either continuously or discontinuously for discrete periods of time, a volatile composition of matter such as a perfume, an air freshener, an air deodorant or the like, is created.

OBJECTS OF THE INVENTION

It is an object of our invention to provide a process for dispensing at a controllable, visibly detectable rate, continuously or discontinuously for discrete and controllable periods of time at steady state volatile compositions of matter from a container into the atmosphere surrounding such container.

It is a further object of our invention to provide an apparatus useful for performing the process for controllably dispensing at a visibly detectable rate, continuously or discontinuously for discrete periods of time, such volatile compositions of matter.

It is a further object of our invention to provide a process for dispensing at a visibly detectable rate, controllably, continuously or discontinuously for discrete periods of time, a perfume or air freshener or other volatile substance from a container into the atmosphere surrounding said container, so that when the effective volatile composition of matter is depleted, the fact of actual depletion as well as the rate of depletion is easily determinable by a person who views the inner void of the apparatus which is instrumental in carrying out the process.

SUMMARY OF THE INVENTION

Our invention defines a process for dispensing in a controllable manner at a visibly detectable rate, continuously or discontinuously for discrete periods of time, at steady state ("0 order"), a volatile composition of matter from a container into the atmosphere surrounding the container and apparatus necessary and useful for carrying out this process. The apparatus includes a hollow totally enclosed structure comprising a thin shell totally enclosing an inner void, the thin shell having a base portion and an upper portion, said base portion having an inner surface:

(i) at least a finite portion of the thin shell being transparent whereby that portion of the inner void which is located proximate to the base portion of the totally enclosed structure is visible from outside the thin shell by a viewer in the presence of visible wavelengths of white light; and visible light;

(ii) contained totally within the inner void of the thin shell and in place on the inner surface of the base portion, a volatile composition temporarily entrapped in an entrapment material and totally entrapped in the entrapment material at least at the instant in time of commencement of the functional operation of the structure (that is, when it is removed from an air-tight package); and (iii) at least a finite section of the thin shell comprising a microporous polymer (preferably containing a plurality of finite solid particles) having a porosity such that when the hollow totally enclosed structure is located in an inert gas at a pressure less than or equal to about 1 atmosphere, the volatile material molecules (e.g., the perfume molecules or the air freshener molecules) are adsorbed onto the inner surface of the microporous polymer section and desorbed from the outer surface of the microporous polymer section at a constant linear velocity and at constant total derivative of concentration of volatile substance within said thin shell with respect to time through the microporous polymer section.

BRIEF DESCRIPTION OF THE DRAWINGS

FIG. 1 is a perspective view of a preferred embodiment of the hollow totally enclosed structure of our invention, with the material of fabrication being flexible polypropylene film.

FIG. 2 is an elevation view of the hollow totally enclosed structure of FIG. 1 shown in cross section with the structure fully loaded with temporarily-entrapped volatile substance.

FIG. 3 is a partial cut-away plan view of the structure of FIG. 1 with the structure fully loaded with volatile substance immediately prior to functional use thereof.

FIG. 4 is a side view of the structure of FIG. 1 shown in cross section with the volatile substance completely spent.

FIG. 5 is a perspective view of a second preferred embodiment of the structure in accordance with our invention with a hollow cylinder fully loaded immediately prior to functional use thereof.

FIG. 6 is an elevation view of the apparatus of FIG. 1 shown in cross section fully loaded with volatile substance immediately prior to functional use thereof, the structure being located within an outer larger air-tight structure, the apparatus containing the entrapped volatile substance not being in functional use.

FIG. 7 is an elevation view of the cylindrical apparatus of FIG. 5 shown in cross section, with the volatile substance being fully loaded in said structure of FIG. 5, the structure of FIG. 5 contained in a larger enclosing cylinder which is air-tight whereby the structure of FIG. 5 is not in functional use.

FIG. 8 is an elevation view of the apparatus of FIG. 5 shown in cross section with the volatile substance previously contained in the cylindrical structure having been fully depleted.

FIG. 9 is an elevation view of another preferred embodiment of our invention, shown in cross section with the volatile substance contained in the structure of our invention being fully loaded in said structure immediately prior to use.

FIG. 10 is an elevation view of the structure of FIG. 9 shown in cross section with the entrapped volatile substance previously contained in said structure having been fully spent.

FIG. 11 is a perspective view of a structure in accordance with our invention where multiple structures (as the individual structure of FIG. 1) are connected to one-another at locations midway between the base portions of each of said structures and the upper portions of each of said structures and along at least portions of the circumferential sealed edges of each of said structures which are sealing the upper portion of each of said structures to the base portion of each of said structures.

FIG. 12 is an elevation view of the structure of FIG. 11 shown in cross section with each of the individual structures of the inter-connected plurality of structures being fully loaded with volatile substance immediately prior to functional use thereof.

FIG. 13 is an elevation view of the apparatus of FIG. 11 shown in cross section with each of the interconnected structures of the structure of FIG. 11 fully loaded with volatile substance prior to use, the plurality of inter-connected structures being contained in an air-tight sealed enclosure structure which has a volume greater than the volume of the plurality of inter-connected sealed structures.

FIG. 14 is a plan view of the plurality of inter-connected structures of FIG. 11.

FIG. 15 is an elevation view of the structure of FIG. 11 which is actually a plurality of inter-connected structures (as the individual structure of FIG. 1), with each of the individual structures containing spent volatile substances immediately subsequent to the last functional use of said structure.

FIG. 16 is a perspective cross-sectional view of the structure of FIG. 11 rolled up and placed in an air-tight cylindrical outer-container when not being used.

FIG. 17 is a perspective view of another preferred embodiment of our invention wherein a plurality of hollow totally enclosed structures are laterally and detachably inter-connected and have a common mid-plane with each of said structures being connected to at least two other of said structures at a location midway between the base portion of each of said structures and the upper portion of each of said structures and along at least a portion of the circumferential sealed edges of each of said structures sealing said upper portions to said base portions. In the embodiment as set forth in FIG. 17, the shape of the individual structures is "heart"-shaped rather than ellipsoidal in shape.

FIG. 19 is a comparative graph showing percent fragrance loss versus time for a structure containing air freshener-containing volatilizable substance as set forth in FIG. 1 versus the same volatilizable substance (air freshener contained in a gel) in the absence of said structure of our invention. (The graph is more particularly described in Example III, infra.)

FIG. 20 represents a graph of rate of fragrance loss versus time for the structure of FIG. 1 for up to one month of use.

FIG. 21 represents an operational graph of rate of fragrance loss versus time for a structure as shown in FIG. 6 wherein the structure of our invention is removed from an outer container for operation and then replaced in the outer container when not in use and the outer container is resealed when not in use. FIG. 21 indicates three separate use (followed by storage) periods for the structure of FIG. 6

FIG. 22 represents a graph of rate of fragrance loss versus time for the entire period of possible continuous use of the structure of FIG. 1 assuming that the structure of FIG. 1 is not replaced at discrete time intervals in an enclosed air-tight outer container.

DETAILED DESCRIPTION OF THE INVENTION

Figure 18:
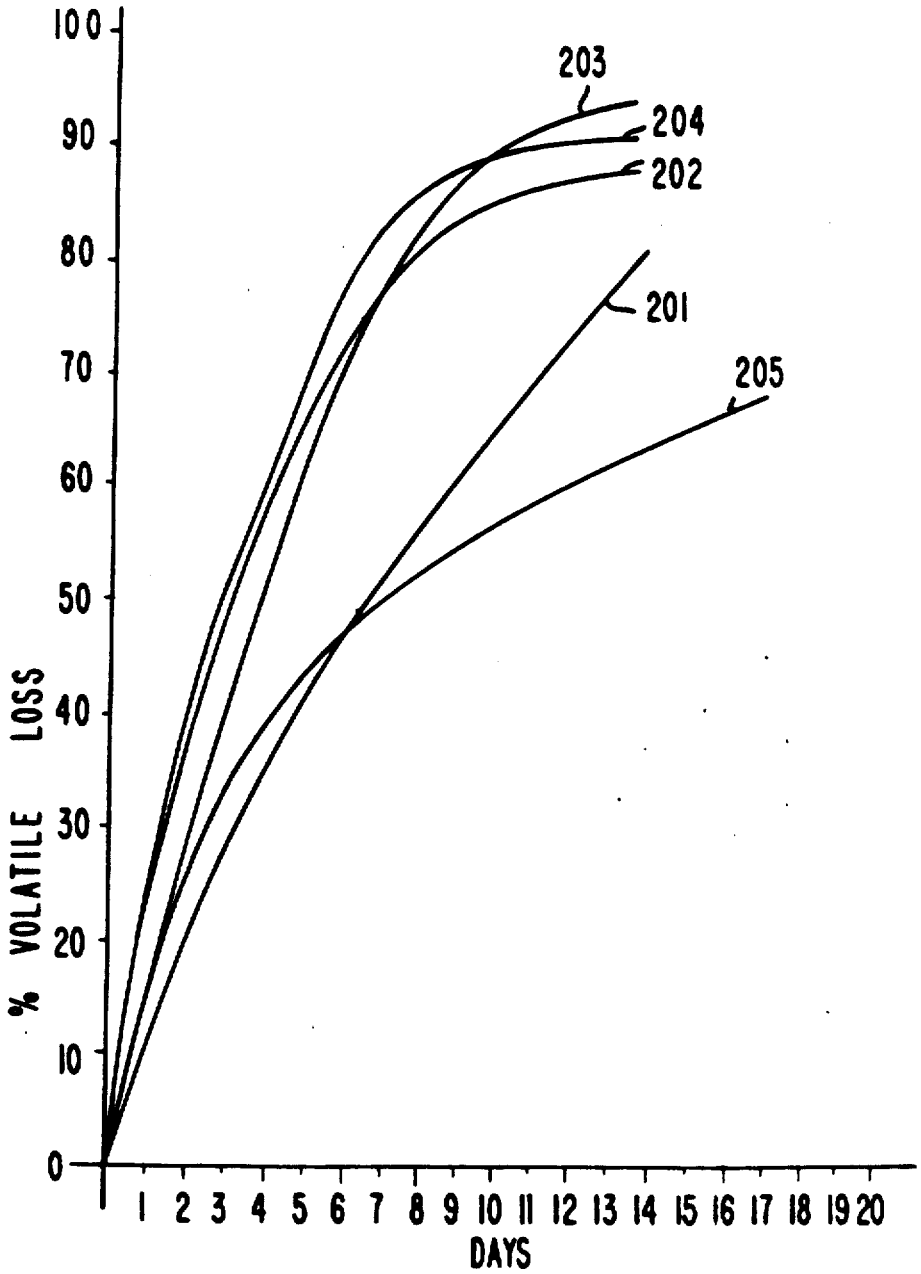
FIG. 18 is a series of graphs of percent volatiles lost versus time comparing the functional use of structures as illustrated in FIG. 1 containing temporarily-entrapped volatilizable substance (air freshener), not containing volatilizable substance (but replaced by ethanol, per se) and standard commercial air fresheners of the prior art as defined according to U.S. Pat. No. 4,014,501. The graphs are more particularly described in Examples I and II, infra.

The process of our invention comprises dispensing at a visibly detectable rate continuously (as illustrated in FIG. 20) or discontinuously for discrete periods of time (as shown in FIG. 21) at steady state, a volatile composition of matter 3 from a container, e.g., as represented by reference numeral 500 in FIG. 1, into the atmosphere surrounding said container. The steps of this process are examplified using structure 500 as follows:

(a) entrapping a volatile composition of matter which may be a perfume composition, an air freshening composition, a deodorizing composition, an animal repellant composition, an insect repellant composition, an insecticide, a herbicide or a pheremone composition or the like, in an entrapment agent whereby a temporarily entrapped volatile composition 3 is formed;

(b) providing a first thin shell section 4 composed of a thin polymeric shell having a curved surface and having an inner void portion, an inner surface and an outer surface and having a first sealable continuous circumferential edge and a first geometric configuration;

(c) placing the entrapped volatile composition 3 in the inner void portion of the first thin shell section and onto the inner surface of the first thin shell section 4;

(d) providing a second thin shell section 2 having a second sealable circumferential edge and a shape and volume which are such that when said second circumferential edge is placed in conforming adjacent edgewise contact with said first sealable circumferential edge, a totally enclosed shell structure 500 is produced with said entrapped volatile composition 3 being totally enclosed within said shell structure leaving a void 6 between said second thin shell section 2 and said volatile substance 3;

(e) placing said second thin shell section 2 having a second sealable continuous circumferential edge which substantially conforms in shape to said first sealable circumferential edge onto said first thin shell section 4 whereby said first sealable edge is in closely fitting sealable proximity with said second sealable edge at location 1;

(f) sealing said first sealable edge to said second sealable edge at location 1 whereby the resultant shell structure enclosing said volatile composition 3 is air-tight except for mass transport of volatile substance through the polymer wall (by adsorption therefrom from void 6 and desorption therefrom into the surrounding atmosphere) with at least a finite section of preferably the second thin shell section being a microporous polymer having a porosity such that when the hollow totally enclosed structure, now sealed, 500, is located in an insert gas at a pressure of less than or equal to about 1 atmosphere, said volatile material molecules diffuse at a constant linear velocity and at a constant total derivative of concentration of volatile substance with respect to time through said microporous polymer section;

(g) optionally, at time intervals of non-use, or for storage purposes, placing the entire shell structure 500 into an outer container 7 which may or may not be transparent and sealing the opening of the outer container at 8 whereby the outer container 7 is air-tight. The outer container 7 prevents the escape of the volatile substance from the entrapment medium into the atmosphere prior to the desired operation of the shell structure and during storage thereof. The outer container 7 has a volume greater than the shell structure which is the functional portion of the apparatus of our invention. The outer container may or may not be transparent or it may be partially transparent.

Examples of the aforesaid microporous polymer compositions of matter are as follows:

(a) Microporous polymers [prepared, for example, according to Canadian Pat. Nos. 1,021,916 or 1,039,911 and U.K. Pat. No. 1,414,785] manufactured by Koninklijke Emballage Industrie Van Leer B.V. of Amstelveen, The Netherlands, [the disclosures of which patents are incorporated by reference herein] for example, a microporous film containing talc having the following specification:

| | |
|---|---|
| Composition | Polypropylene + filler |

-continued

| | |
|---|---|
| Thickness | 100 ± [milli]microns |
| Weight | ±90 g/m$^2$ |
| Ultimate tensile strength | 30 MN/m$^2$ (machine direction)<br>11 MN/m$^2$ (transverse direction) |
| Elongation at break | 180% (machine direction)<br>350% (transverse direction) |
| Pore size | 0.2 [milli]microns[(mas)] *(max)* |
| Void volume | .34 cm$^3$/g (30%) |
| Density | ±900 kg/m$^2$ |
| Air flow | 3 cm$^3$/cm$^2$/min at 1 kg/cm$^2$ |
| Water flow | 0.001 cm$^3$/cm$^2$/min at 1 kg/cm$^2$ |
| Air resistance (Gurley) | 10$^4$ secs. |
| Water vapour transmission | 150 g/m$^2$/24 hrs at 23° C.<br>50% rh |
| Thermal stability | 10 hrs at 130° C. |

[(b) Thin microporous films produced from Surlyn® resin as described in Examples 362, 363, 364, 365 and 366 at columns 45 and 46 of U.S. Pat. No. 4,247,498 the disclosure of which patent is incorporated by reference herein;]

[(c) A microporous polymer membrane produced according to Example 10 of U.S. Pat. No. 4,226,944 which is a polyurethane resin containing a particulate filler except that the fragrance set forth therein is not initially (prior to functional use) contained in the microporous polymer shell, but is only initially (prior to functional use) contained in the porous retention entrapping sponge or gel 3 in FIG. 2; or 11 in FIG. 5; or 19 in FIG. 9;B]

[(c-bis) A microporous polymer prepared according to U.S. Pat. No. 4,239,714, the abstract for which is set forth below:]

[The pore size distribution of a microporous sepn medium (I) is modified by filling its pores with a volatile liq. A controlled amt of the volatile liq is evaporated to lower the level of the liq within the pores to below the bulk surface of (I) and thereby form voids at the entraces to the pores.]

[A conc. soln of a pore blocking agent is applied to the bulk surface of (I). The pore blocking agent is insoluble in the volatile liq and capable of being insolubilised in its soln. Its molecular size distribution has a predetermined lower limit so that it only enters pores larger than that. Excess pore blocking agent is removed from the surface of (I); that which remains is insolubilised to immobilise it in the pores.]

[The pore blocking agent obstructs the entrances to all pores larger than a certain size so that (I) has a sharp cut-off in the max molecular size it passes. (I) can be a polymeric membrane or chromatographic gel used to separate proteins, enzymes, viruses and immunological active fragments by ultrafiltration, dialysis electrodialysis, electrophoresis or gel permeation or gel exclusion chromatography.]

[(d) A membrane produced according to Japanese Application No. J5-5081,655 assigned to Kureha Chemical Industries KK and published on June 19, 1980, containing a water soluble polyvinyl alcohol having a molecular weight of 12,000, intimately admixed with xanthan gum, the ratio of polyvinyl alcohol:xanthan gum being 6:4 (weight:weight);]

[(e) A cyclodextrin microporous film containing activated silicate as prepared according to Japanese published Application No. J5-5078,965 assigned to Kokando KK and published on June 14, 1980;]

[(f) A microporous polyurethane specifically as described in German Offenlegungsschrift No. 2,324,314 published on Nov. 29, 1973 and assigned to Teijin Cordley Ltd. (abstracted in Chem. Abstracts Volume 81, 1974 at section 4589u).]

Insofar as the microporous film is concerned, it is preferred that a filler be incorporated therein having an average particle size of from about 0.3 up to about 500 microns. In the event that a filler is not contained, the pore size of the microporous polymer must be smaller than if a filler is contained by 3 or 4 orders.

Particulate or pulverulent fillers which are useful in the practice of this invention include, but are not limited to, clays, including both untreated clays and those which have been surface-treated in various ways well known in the art, ground limestone, talc, precipitated calcium carbonate, including surface-treated types, alumina, aluminium silicate, barytes, wollastonite or other calcium silicate, silica, zirconia, titanium dioxide, soap and synthetic detergents in solid form.

The synthetic detergent can be, for example, an alkylaryl sulphonate detergent, such as a sodium alkyl benzene sulphonate or sodium alkyl naphthalene sulphonate. Where the sulphonate used is an alkyl benzene sulphonate, the benzene ring of the sulphonate preferably has only 1 allyl substituent and such substituent contains from 8 to 18 carbon atoms. Among such alkyl benzene sulphonates are sodium linear dodecylbenzene sulphonate, sodium tridecylbenzene sulphonate and sodium nonylbenzene sulphonate. On the other hand, where the sulphonate used is an alkyl naphthalene sulphonate, the naphthalene ring of the sulphonate perferably has 1 or 2 alkyl substituents and the total number of carbon atoms in the alkyl substituents is from 3 to 10. Among such sulphonates are sodium monoisopropylnaphthalene sulphonate, sodium diisopropylnaphthalene sulphonate, sodium diamylnaphthalene sulphonate and sodium monocaprylnaphthalene sulphonate. The sulphonates in solid form are commercially available in 40% to 90% by weight active form, the rest being predominantly sodium sulphate. In practicing the present invention, it is preferable to use the 90% active form, which is the highest available commercially, but other forms can also be used.

Useful clay fillers are described in U.S. Pat. No. 3,080,256 and are compositions which can be prepared by a procedure involving coating kaolin with a small amount (for example, from 0.2% to 2% by weight, based on the weight of the kaolin) of a polyamine, e.g. ethylene diamine, hexamethylene diamine, tetraethylene diamine, diethylene triamine, tetraethylene pentamine and guanidine.

Other useful clay fillers are described in U.S. Pat. No. 3,151,993 and can be prepared by a procedure involving coating kaolinite particles with aluminum hydroxide precipitated in situ at a pH from 7.5 to 9. We prefer to use clay, limestone, soap, linear dodecylbenzene sodium sulphonate, combinations of clay and linear dodecylbenzene sodium sulphonate, or combinations of clay and soap. Other particulate or pulverulent fillers can also be used. The only limitations are that the fillers should not adversely affect or react with the aromatizing substance or entrapping material entrapping the aromatizing substance used or absorb the aromatizing material to such a degree that release from the microporous polymer is unduly inhibited or entirely prevented.

Although the particle size of the filler can be varied over a wide range, 0.3 microns up to 500 microns, extremely coarse particles are generally undesirable because they may detract from the aesthetic qualities of the finished microporous polymer.

The amount of filler can be varied over a wide range depending on the amount of volatilizing material to be released from entrapped volatilizable substance 3 and the viscosity of the aromatization material which is adsorbed onto and desorbed from the microporous polymer. We have found that filler levels in a range of from 5 to 100 parts by weight per 100 parts of polymer are generally satisfactory, although greater or less amounts can be used if desired.

Any type of aromatizing substance, e.g., air freshener, can be used in the practice of this invention provided that it does not react with any component of the microporous polymer or polymer or other substance used in fabricating the outer shell of the structure of our invention. Fragrances are usually complex mixtures and no component of the desired fragrance should be reactive with any component of the microporous polymer or any other component which is used to fabricate the shell structure of our invention.

[Insofar as the microporous film produced in accordance with U.S. Pat. No. 4,247,498 is concerned, this microporous film is produced by heating a mixture of synthetic thermoplastic polymer which may be a polymer or a copolymer of an ethylenically unsaturated monomer, condensation polymer, polyphenylene oxide or a blend thereof and a compatible liquid to a temperature and for a time sufficient to form a homogeneous solution; allowing the solution to assume a desired shape (in this case, film or thin shell polymer) and cooling the solution to initiate liquid-liquid phase separation and form at substantially the same time a plurality of liquid droplets of substantially the same size in the continuous liquid polymer phase, continuing the cooling to solidify the polymeric film and removing substantially all of the liquid resulting to form a polymer structure which is a three-dimensional microporous cellular structure comprising a plurality of substantially spherical microcells having an average diameter (C) from about 0.05 to about 100 microns (more preferably 0.05 to 15 microns) distributed substantially uniformly throughout the structure, adjacent cells being interconnected by pores smaller in diameter than the microcells, the pore size distribution expressed by S having a value in the range of from 0.01 to 30 microns, the log ratio (Naperian base) of the average cell diameter (C) to the average pore diameter (P) having a value in the range of from 0.2 to 2.4 and the log ratio (Naperian base) of the pore size distribution expressed by (S) to the average cell diameter (C) having a value in the range of from −1.4 up to 1.0, the pores and the cells being a void and the polymer being a synthetic thermoplastic polymer which is a polymer or copolymer of an ethylenically unsaturated monomer, a condensation polymer, a polyphenylene oxide or a blend thereof. Preferably, the polymer phase and compatible liquid have intimately admixed therewith the aforedescribed filler in proportion ranges stated, supra.]

When the structure of our invention is ready to be used in dispensing at a steady state, and at a visibly detectable rate continuously or discontinuously for discrete periods of time from container 500, the container 500 is removed from outer container 7 and maintained in any convenient area or 3-space. FIG. 4 illustrates the container 500 in cross section after the entrapped volatile material is totally depleted as a result of the steady state mass transport of the volatile substance through microporous polymer section of a portion of the container wall, e.g., preferably wall 2. The fully depleted substance is shown in FIG. 4 as indicated in reference numeral 5.

If desired, as an additional embodiment of this invention, each of the shell structures of our invention may be interconnected as shown in FIGS. 11, 12, 13, 14, 15, 16 and 17 as structures 504, 505 and 506. Thus, a plurality of hollow totally enclosed structures, having upper portions 23A, 23B, 23C, 23D, 23E, 23F, 23G, 23H and 23J are laterally and detachably interconnected, having a common midplane 22A, each of said structures being connected to at lease two other of said structures, for example in structure 504, at a location midway between the base portion of each of said structures and the upper portion of each of said structures, with the base portion and upper portion of three of said interconnected structures shown in FIG. 12, to wit: the upper portions as 23C, 23D and 23J and the lower portions shown as 29C, 29D and 29J.

In constructing such a structure as structure 504 in FIGS. 11, 12, 13, 14, 15, 16 and 17, the upper polymeric portion containing upper portions 23A, 23B, 23C, 23D, 23E, 23F, 23G, 23H and 23J having a sealable circumferential edge 22A is sealed to a diametrically opposed lower portion containing such lower portions as 29C, 29D and 29J at sealable circumferential edge 22B with sealable circumferential edges 22A and 22B being in closely fitting sealable proximity with one another whereby when they are sealed, an air-tight connection is produced with the only means of ingress and egress from the voids 27C, 27D and 27G for the volatile substances contained in 26C, 26D and 26J being through microporous polymer sections in upper shell portions 23C, 23D, 23J and the like, and/or lower portions 29C, 29D and 29J and the like.

When such a structure as structure 504 as illustrated in FIGS. 11, 12, 13, 14, and 15 are produced, they may be stored while not in use in a container such as container 24 as illustrated in cross section in FIG. 13 or they may be rolled up and stored in container 505 as illustrated in FIG. 16. Conveniently, the container 505 in FIG. 16 is cylindrical in shape and has a closure which is in the form of a screw top which may be easily removed and replaced for the purposes of storing structure 504 while not in use. When structure 504 is stored while not in use, the pressure within container 505 and without structure 504 and within structure 504 is equalized so that during storage no mass transfer from such entrapped volatile substance material as 26C, 26D and 26J takes place into the outer atmosphere.

After the structure 504 is removed from the outer container such as container 24 or container 505, it is then placed in an appropriately convenient place and the volatile substance is depleted from such substances as 26C, 26D and 26J until such point as the totally depleted substance is visible from without structure 504 and is shown to be depleted as illustrated in FIG. [16] *15* (as reference numerals 28C, 28D and 28J). Thusly, the void 27C, 27D and 27J is fully visible from outside the structure in the presence of the visible wavelengths of light (e.g., white light) so that the depleted substance 28C, 28D and 28J whether it be a gel or microencapsulated material or sponge material, is easily visible.

FIG. 17 illustrates a variation of structure 504 as structure 506 wherein the individual structures may be separated for individual use at 507, with the shape of the upper portion of each of the individual structures indicated as a "heart" shape at 508.

Comparative operation of structure 500 with perfumed fragrance entrapped material or ethyl alcohol entrapped material at 3 with material 3 in prior art apparatus (e.g., that described in U.S. Pat. No. 4,014,501) is set forth in FIG. 18. The graphs shown by reference numerals 201 and 203 represent the operation of structure 500 (percent volatile substance loss versus time) without any perfume material contained within the entrapped volatile substance 3 [buy] *but* only containing ethyl alcohol entrapped in gel 3. The graphs shown by reference numerals 202 and 204 (percent perfume lost versus time) indicate the rate of release versus time using structure 500 when employing 2% fragrance in a gel indicated by reference numeral 3 with the microporous polymer in structure 500 [for reference numbers 201, 202, 203 and 204 being that described in Canadian Pat. Nos. 1,039,911 and 1,021,916 and U.K. Pat. No. 1,414,785 whereby] specially compounded polypropylene film with talc is used, having the following specifications:

| | |
|---|---|
| Composition | Polypropylene + filler |
| Thickness | 100 ± [milli]microns |
| Weight | ±90 g/m$^2$ |
| Ultimate tensile strength | 30 MN/m$^2$ (machine direction)<br>11 MN/m$^2$ (transverse direction) |
| Elongation at break | 180% (machine direction)<br>350% (transverse direction) |
| Pore size | 0.2 [milli]microns (max) |
| Void volume | .34 cm$^3$/g (30%) |
| Density | ±900 kg/m$^2$ |
| Air flow | 3 cm$^3$/cm$^2$/min at 1 kg/cm$^2$ |
| Water flow | 0.001 cm$^3$/cm$^2$/min at 1 kg/cm$^2$ |
| Air resistance (Gurley) | 10$^4$ secs. |
| Water vapour transmission | 150 g/m$^2$/24 hrs at 23° C.<br>50% rh |

as manufactured by Koninklijke Emballage Industrie Van Leer B.V. of Amstelveen, The Netherlands.

In each of the graphs wherein perfumed material is used, it is apparent that for the major portion of the useful life of the structure, e.g., structure 500, the rate of mass transport of perfume substance, when in use, is "0" order, that is:

$$\frac{dc}{dt} = k$$

wherein k is a constant.

Discussion covering the preparation of the compositions of matter which constitute the fragranced gels and unfragranced gels whereby the graphs as represented by reference numerals 201, 202, 203, 204 and 205 of FIG. 18 are prepared is set forth in Examples I and II, infra.

By the same token, in FIG. 19, the graph indicated by reference numeral 302 indicates percent fragrance loss versus time for an air freshener gel containing 2% by weight fragrance but not enclosed in a structure defined according to our invention. It will be noted that the diffusion of the air freshener is in accordance with ordinary diffusion laws and is not steady state, to wit:

$$\frac{\partial C_A}{\partial t} = D\left\{\left(\frac{\partial^2 C_A}{\partial x^2}\right)_{yz} + \left(\frac{\partial^2 C_A}{\partial y^2}\right)_{zx} + \left(\frac{\partial^2 C_A}{\partial z^2}\right)_{xy}\right\}$$

On the other hand, the graph indicated by reference numeral 301 in FIG. 19 is for the same air freshener gel 3 containing 2% by weight fragrance (as more particularly described in Example III) located in the thin shell structure of our invention as illustrated in FIGS. 1, 2 and 3. The depleted air freshener gel is shown by reference numeral 5 in FIG. 4 (the depletion being at the end of a 55 day period as shown on the graph indicated by reference numberal 301 in FIG. 19).

FIGS. 20 and 21 show, respectively, continuous and discrete usages of the shell structure as illustrated in FIG. 1. FIG. 20 is a graph of (dc/dt) versus time; wherein during the first five minutes of operation, the mass transfer rate is described as unsteady state until a "steady state" condition is reached wherein (dc/dt) is a constant for at least one month (until depletion as shown in FIGS. 4 and 8).

In FIG. 21, (dc/dt) is a constant after the first five minutes of usage until the time that the shell structure of our invention as shown in FIG. 1 is placed into an outer container as shown in any one of FIGS. 6, 7 or 16.

FIG. 22 is a graph of (dc/dt) versus time wherein the period of from $t_0'''$ to $t_1'''$ is a condition of "unsteady state" mass transport (usually no more than a few minutes) and the period from $t_1'''$ to $t_\omega'''$ is a condition of "steady state" mass transport; a very long period of time, e.g., 55–75 days and even longer.

The "steady state" adsorption/desorption of volatile substance mass transport mechanism onto and from the microporous polymer section of the shell structure of our invention may be set forth in the form of a mathematical model as taught by Adamson "Physical Chemistry of Surfaces" Second Edition, Interscience Publishers, 1967, as follows:

$$n_2^s\,(\text{apparent}) = n_0 \Delta N_2^l$$

$$\Gamma_2^s = (n^s/\Sigma)(N_2^s - N_2^l)$$

$$\Gamma_2^s = (n^s/\Sigma)(n_2^s/n^s - n_2^l/n^l)$$

$$\Gamma_2^s = (n_0/\Sigma)(N_2^0 - N_2^l) = n_0 \Delta N_2^l/\Sigma$$

$$\Gamma_2^s = n_0 \Delta N_2^l/\Sigma = (n_2^s N_1^l - n_1^s N_2^l)/\Sigma$$

$$N_2^s = N_2 \frac{K}{1 + (K-1)N_2}$$

$$\Gamma_2^s = (n^s/\Sigma)\frac{(K-1)N_1N_2}{1 + (K-1)N_2}$$

$$N_1N_2/n^0\Delta N_2 = 1/n^s(K-1) + (1/n^s)N_2$$

$$\Sigma\Gamma_2^1 = n_2^s - n_1^s(N_2/N_1) = n^s(N_2^s - N_1^sN_2/N_1)$$

$$\Sigma\Gamma_2^1 = (n^s/N_1)(N_2^s - N_2)$$

$$\Gamma_2^1 = \Gamma_2^s/N_1 = n_0\Delta N_2/\Sigma N_1$$

$$\Gamma_2^1 = (n^s/\Sigma)\{[(K-1)N_2]/[1 + (K-1)N_2]\}$$

$$\theta = (K-1)N_1N_2/[1 + (K-1)N_2] = (K-1)N_1N_2/(N_1 + KN_2)$$

$$\theta = KN_2/(N_1 + KN_2) - N_2$$

wherein the terms with the superscript "s" refer to components in the adsorbed layer and the terms with the superscript "1" refer to terms in solution; the terms with the subscript "1" refer to a "first" component and the terms with subscript "2" refer to a "second" component; with "N" referring to mole fraction and "n" referring to number of moles and with $\Gamma$ being indicative of "surface excess"; "K" being indicative of equilibrium constant and $\Sigma$ representing the sum total of the moles on the adsorbed layer.

Another embodiment which is preferred for the practice of our invention involves the use of a rigid rather than flexible polymer in forming rigid cylindrical containers useful for the process of our invention as illustrated in FIGS. 5, 7, 8, 9 and 10.

The process of our invention for dispensing at a controllable and visibly detectable rate, continuously or discontinuously, for discrete periods of time a volatile composition of matter from a cylindrical container 501 into the atmosphere surrounding the container in this particular embodiment comprises the steps of:

A. Entrapping the volatile composition of matter, e.g., perfume, in an entrapment agent (the entrapped material being indicated by reference numeral 11) whereby a temporarily entrapped volatile composition is formed;

B. Placing the entrapped volatile composition 11 within cylinder 501 (that is, a first thin shell section thereto). The top of the cylinder 101 and the bottom of the cylinder 102 may be fabricated from a transparent non-porous polymer (that is, a polymer which is not porous to the volatilizable substance) whereby the inner void of the cylinder can be viewed from the outside of the container so that one can easily ascertain when the entrapped volatile substance, 11 is depleted (as shown by reference numeral 16 in FIG. 8). The side wall of the cylinder 12 may be fabricated from a microporous polymer [such as that described in Canadian Pat. No. 1,039,911 or United Kingdom Pat. No. 1,414,785 assigned to Koninklijke Emballage Industrie Van Leer B.V. or can be produced of microporous polymers which are laminated such as that described in Israel Pat. No. 52650 assigned to Koninklijke Emballage Industrie Van Leer B.V.] wherein, for example, the polymer [is microporous and] contains a talc filler.

When not in use, the cylinder 501 containing entrapped volatile substance 11 is preferably placed in an outer cylindrical container 502 as shown in FIG. 7. The outer cylindrical container is referred to by reference numeral 502 in FIG. 7. The outer cylindrical container has a removable cap 14 which may be screwed at 103 into the lower portion 13 of said outer container 502. When the cylinder 15 is in use, the screw top 14 is removed and the inner container 15 containing the entrapped volatile composition 11 may remain in place within the outer container 502 or may be removed to a more convenient location for use. Not all of the side wall 12 need be fabricated of microporous polymer. Indeed, merely the upper third or the upper quarter or the lower quarter of the side wall or even the top or the bottom of the cylindrical container may be fabricated from microporous polymer, the remainder of the container 15 shell being fabricated using a transparent substance which is rigid or flexible or using a silicate or quartz glass.

Another embodiment of the cylindrical hollow structure which is illustrative of our invention is set forth in FIGS. 9 and 10 wherein the upper portion of the cylindrical structure 17 may be screwed into the lower portion of the structure 18 at screw threads 20. Thus, structure 503 containing volatile substance 19 may be manufactured in a form which is reusable when the volatile substance 19 is depleted down to the remaining depleted gel (or other entrapment substance) 21 as indicated in FIG. 10. Conveniently, lower portion 18 may be fabricated from a transparent substance such as transparent rigid polypropylene or glass and upper portion 17 may be fabricated from microporous polyurethane or polypropylene containing talc and may be perpetually opaque or opaque only when cylinder 503 is not in use. Thus, when volatile substance 19 is depleted down to depleted substance 21 (as illustrated in FIG. 10), the upper portion 17 of cylinder 503 in FIGS. 9 and 10 may be temporarily removed and additional substance 19 may be added to the lower portion 18. Structure 503 in FIGS. 9 and 10 may then be replaced into a larger cylinder to form a structure such as that illustrated in FIG. 7, the purpose of which is for storage; until it is decided to reuse the structure 503.

The rate of mass transport of volatile substance from cylinder 501 or from cylinder 503 is over substantially the entire period of presence of volatile substance in entrapment composition, "steady state" or constant. Thus, although the general mass transport equation is:

$$N_A = -D_{AB} \cdot \frac{\partial C_A}{\partial y}$$

wherein $N_A$ is the molar rate of mass transport per unit area; $D_{AB}$ is the "diffusivity" of A in B, a physical property of the volatile vapor and the adsorbing polymer, $C_A$ is the molar concentration of A in the void space immediately within the shell; and y is the thickness of the adsorbing and desorbing polymer. For the purpose of our invention $N_A$ is a constant and is not a function of time during the operation of the hollow totally enclosed structure of our invention. Indeed, when operating in several directions, the equation for mass transport of volatile substance is:

$$\frac{\partial C_A}{\partial t} = D\left\{\left(\frac{\partial^2 C_A}{\partial x^2}\right)_{yz} + \left(\frac{\partial^2 C_A}{\partial y^2}\right)_{zx} + \left(\frac{\partial^2 C_A}{\partial z^2}\right)_{xy}\right\}$$

wherein $(\partial C_A/\partial t)$ is a constant.

The following examples serve to illustrate embodiments of our invention as it is now preferred to practice it with reference to using air freshener/perfume compositions in conjunction with the hollow totally enclosed structures of our invention as illustrated FIGS. 1, 5 and 9. It will be understood that these examples are illustrative and that the invention is to be restricted thereto only as defined in the appended claims.

EXAMPLE I

Into compartment 6, onto surface 4 of the structure 500 illustrated in FIGS. 1, 2 and 3 is placed a composition prepared as follows: 3.0 parts by weight of Carbopol ® 940 (manufactured by the B. F. Goodrich Company) (see Note 1) is sifted into the vortex of rapidly stirring water (88.8 parts by weight) containing 0.2 parts by weight of methyl paraben. The mixing is continued until a smooth cloudy dispersion is formed. 2.0 parts by weight of a perfume composition (see Note 2) is added to the prepared slurry and the slurry is continued to be mixed until the perfume composition is dispersed. The slurry is then neutralized with 6.0 parts by weight of diisopropanolamine (50% solution in water) using slow mixing to avoid the inclusion of air. The structure 500 is then sealed along the circumferential edges at location 1 as shown in FIGS. 1, 2 and 3 and use of the structure resulting therefrom is shown in accordance with the graph referenced by reference numeral 202 in FIG. 18. When instead of the perfume (Note 2), only ethyl alcohol is used as the volatilizable material, the operation of structure 500 is in accordance with the graph indicated by reference numeral 201 in FIG. 18. It will be noted that for periods of use, structure 500 operates at steady state very soon after (5 minutes) use is commenced.

Note 1: Carbopol ® 940 is produced by the B. F. Goodrich Chemical Company of 3135 Euclid Avenue, Cleveland, Ohio. It is identified as a carboxyvinyl polymer of high molecular weight.

Note 2: The formulation of the fragrance is as follows:

| Ingredients | Parts by Weight |
|---|---|
| Para cresol | 1 |
| Methyl jasmonate | 100 |
| Acetyl methyl anthranilate | 20 |
| Farnesol | 4 |
| Cis-3-hexenyl benzoate | 30 |
| Nerolidol | 30 |
| Indol | 15 |
| Eugenol | 20 |
| Benzyl alcohol | 40 |
| Methyl linoleate | 40 |
| Jasmin lactone | 20 |
| Dihydromethyl jasmonate | 10 |
| Linalool | 150 |
| Benzyl acetate | 400 |
| Abietyl alcohol | 150 |
| Cis jasmone | 150 |

The evaporating surface in hollow structure 500 is 8 square inches; and the weight of entrapped volatile substance 3 is 30 grams.

EXAMPLE II 3.0 parts by weight of Carbopol ® 940 (manufactured by the B. F. Goodrich Company) is sifted into the vortex of 44.4 parts rapidly stirring ethyl alcohol and 44.4 parts of distilled water. Mixing is continued until a smooth, cloudy dispersion is formed. 2.0 parts by weight of the perfume of Example I is then added to the prepared slurry and mixing is continued until the perfume is dispersed. The slurry is then neutralized with 6.0 parts by weight of diisopropanolamine (50% solution in water) using slow mixing to avoid inclusion of air. The resulting gel is then placed into cylinder 501 of FIG. 5. The use of this air freshener cylinder is in accordance with the graph indicated by reference numeral 204 in FIG. 18. Without the use of the perfume composition of Example I, the cylindrical shell of FIG. 5 operates in accordance with the graph indicated by reference numeral 203 in FIG. 18. In both cases, the percent volatiles lost during Example I (but using ethanol, instead), the cylindrical shell of FIG. 5 operates in accordance with the graph indicated by reference numeral 203 in FIG. 18. In both cases, the percent volatiles lost during operation of the cylinder 502 is in accordance with a steady state mass transport mechanism can be observed from the graphs 201, 202, 203 and 204 of FIG. 18.

When the gel of this example is simply used in a commercial air freshener (in the air freshener of U.S. Pat. No. 4,014,501), the mass transport mechanism is "unsteady state" in accordance with the graph indicated by reference numeral 205 in FIG. 18.

EXAMPLE III 83.45 grams of distilled water is heated to 85° C. With rapid agitation on a propeller type mixer, Gelcarin ® AFG-15 (carageenan prepared by the Marine Colloids Corporation) is dispersed in the water. 3.50 grams of glycerine is slowly added to the carageenan dispersion. The mixture of glycerine and carageenan is then reheated and combined with 2.0 parts by weight of the perfume composition of Example I and 8.00 parts by weight of Tween ® 80 (a trademark of I.C.I. America) (see Note 3). 0.05 parts by weight of formaldehyde is then added to the resulting mixture slowly and the resulting material is then poured into the cylinder of FIG. 9. It is material is then poured into lower portion 18 of cylinder 503 of FIG. 9. The lower portion 18 of cylinder 503 is then sealed at 20 with upper portion 17 and placed in use.

Note 3: Tween ® 80 is a mixture of oleate esters of sorbitol and sorbitol anhydrides consisting predominantly of the monoester condensed with approximately 20 moles of ethylene oxide in accordance with the formula:

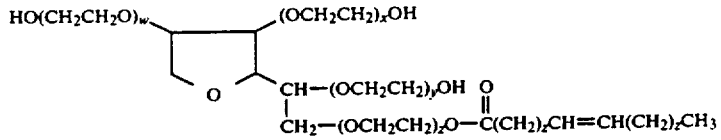

wherein $w+x+y+z$ has an average value of 20.

The graph indicated by reference numeral 301 indicates the length of time of usefulness of the resulting cylinder; a "steady state" mass transport mechanism for the use of cylinder 503 as an air freshening apparatus.

When the composition prepared above is used in accordance with a standard air freshener package (per U.S. Pat. No. 4,014,501), the rate of fragrance loss is shown in accordance with the graph indicated using reference numeral 302 in FIG. 19 (an unsteady state mass transport mechanism rather than the steady state mass transport mechanism of graph 301 in FIG. 19).

What is claimed is:

[1. A hollow totally enclosed structure comprising a thin shell totally enclosing an inner void, said thin shell having a base portion and an upper portion, said base portion having an inner surface:

(i) at least a finite portion of said thin shell being transparent whereby that portion of said inner void which is located proximate to the base portion of said totally enclosed structure is visible from without said thin shell, in the presence of visible wavelengths of light;

(ii) contained totally within the said inner void of said thin shell and in place on said inner surface of said base portion, a volatile composition temporarily entrapped and totally entrapped at least at the instant in time of commencement of functional operation of said structure, in an entrapment material, said volatile composition being selected from the group consisting of perfume compositions, herbicide compositions, insecticide compositions, animal repellant compositions, air freshener compositions, pheremone compositions, odor maskant compositions, deodorant compositions and insect repellent compositions;

(iii) at least a finite section of said thin shell comprising a microporous polymer and termed "a microporous polymer shell section" having a porosity such that when said hollow totally enclosed structure is located in an inert gas at a pressure of less than or equal to about 1 atmosphere, said volatile material molecule are transported at a constant linear velocity and at a constant total derivative of concentration of volatile substance with respect to time onto the inner surface of said microporous polymer section via an adsorption mechanism and from the outer surface of said microporous polymer section to the surrounding atmosphere via a desorption mechanism.]

[2. The hollow totally enclosed structure of claim 1 wherein said base portion is non-porous and transparent and said upper portion is a microporous polymeric membrane and is opaque at least at the instant in time of commencement of the functional operation of said structure, said base portion being sealed to said upper portion.]

[3. The hollow totally enclosed structure of claim 2 wherein said upper portion consists of a microporous polymeric membrane which consists essentially of a polyolefin intimately admixed with a powder having an average particle diameter of from about 0.3 up to about 500 microns.]

[4. The hollow totally enclosed structure of claim 1 wherein the microporous polymer is a microporous polymeric membrane consisting of a polyurethane foam containing a particulate filler having an average particle diameter of from about 0.3 up to about 500 microns, said polyurethane foam formed by reacting a liquid polyol with at least one organic polyisocyanate, water and at least one catalyst.]

[5. The hollow totally enclosed structure of claim 1 wherein said microporous polymer is a 3-dimensional microporous cellular polymer structure comprising a plurality of substantially spherical microcells having an average diameter (C) of from 0.05 to 100 microns distributed substantially uniformly throughout the structure, adjacent cells being interconnected by pores smaller in diameter than the microcells, the pore size distribution expressed by (S) having a value in the range of from 0.01 to 30 microns, the Naperian base log ratio of the average cell diameter (C) to the average pore diameter (P) having a value in the range of from 0.2 to 2.4 and the Naperian base log ratio of the pore size distribution expressed by (S) to the average cell diameter (C) having a value in the range of from −1.4 to 1.0, the pores and the cells being void at the instant in time of commencement of the functional operation of said structure and the polymer being a synthetic thermoplastic polymer which is a polymer or copolymer of an ethylenically unsaturated monomer, a condensation polymer, a polyphenylene oxide or a blend thereof.]

[6. The hollow totally enclosed structure of claim 1 which is in the shape of a cylinder, the ends of the cylinder being translucent and non-porous and the side of said cylinder being opaque at least at the instant in time of commencement of the functional operation of said structure, said side consisting of a microporous polymeric structure.]

[7. The hollow totally enclosed structure of claim 3 wherein the thickness of the microporous polymer is about 100 millimicrons; the pore size is approximately 0.2 millimicrons; the void volume of the microporous polymer is approximately 34 cubic centimeters per gram and the density is approximately 900 kilograms per cubic meter.]

[8. A structure comprising (a) a first hollow totally enclosed structure defined according to claim 1 and enclosing said first structure, (b) a second air-tight totally enclosed structure, said first totally enclosed structure having a volume less than said second air-tight totally enclosed structure, said first totally enclosed structure being of such dimensions that it is (i) enclosable within said second air-tight totally enclosed hollow structure, and (ii) the internal volume of said second air-tight totally enclosed hollow structure is greater than the external volume of said first hollow totally enclosed structure.]

[9. A structure defined according to claim 1 wherein (i) said base portion comprises a first thin polymer shell having a curved surface and an inner void portion and an inner surface and an outer surface and a first sealable continuous circumferential edge; (ii) said upper portion comprises a second thin shell section having a second sealable continuous circumferential edge which substantially conforms in shape to said first sealable circumferential edge and (iii) said base portion is sealed by means of a continuous seal at the said first circumferential edge thereof to said upper portion at the said second circumferential edge thereof.]

[10. A structure defined according to claim 2 wherein (i) said base portion comprises a first thin polymer shell having a curved surface and an inner void portion and an inner surface and an outer surface and a first sealable continuous circumferential edge; (ii) said upper portion comprises a second thin shell section having a second sealable continuous circumferential edge which substantially conforms in shape to said first sealable circumferential edge and (iii) said base portion is sealed by means of a continuous seal at the said first circumferential edge thereof to said upper portion at the said second circumferential edge thereof.]

[11. A structure defined according to claim 3 wherein (i) said base portion comprises a first thin polymer shell having a curved surface and an inner void portion and an inner surface and an outer surface and a first sealable continuous circumferential edge; (ii) said upper portion comprises a second thin shell section having a second sealable continuous circumferential edge which substantially conforms in shape to said first sealable circumferential edge and (iii) said base portion is sealed by means of a continuous seal at the said first circumferential edge thereof to said upper portion at the said second circumferential edge thereof.]

[12. The structure claimed according to claim 1 wherein the driving force of the molecular mass transfer of the volatile substance from within the hollow totally enclosed structure to the atmosphere surrounding said structure on operation thereof results from (a) a difference in the pressure between the gas phase of the inner void of said shell and the gas phase-containing 3-space immediately adjacent the outer surface of said microporous polymer shell section and (b) the steady state desorption of the liquid phase of the volatile substance present in the microporous polymer into the gas phase-containing 3-space immediately adjacent the outer surface of said microporous polymer shell section and (c) the steady state absorption of the liquid phase of volatile substance present in a microporous polymer from the gas phase within the inner void of said shell onto the inner surface of said microporous polymer shell section.]

[13. A plurality of hollow totally enclosed structures laterally and detachably interconnected having a common midplane, each of said structures being defined individually according to claim 9, each of said structures connected to at least one other of said structures (i) at a location midway between the base portion of each of said structures and the upper portion of each of said structures and (ii) along at least a portion of the circumferential sealed edge of each of said individual structures sealing said upper portion to said base portion of each of said individual hollow totally enclosed structures.]

[14. A plurality of hollow totally enclosed structures laterally and detachably interconnected having a common midplane, each of said structures being defined individually according to claim 10, each of said structures connected to at least one other of said structures (i) at a location midway between the base portion of each of said structures and the upper portion of each of said structures and (ii) along at least a portion of the circumferential sealed edge of each of said individual structures sealing said upper portion to said base portion of each of said individual hollow totally enclosed structures.]

[15. A plurality of hollow totally enclosed structures laterally and detachably interconnected having a common midplane, each of said structures being defined individually according to claim 11, each of said structures connected to at least one other of said structures (i) at a location midway between the base portion of each of said structures and the upper portion of each of said structures and (ii) along at least a portion of the circumferential sealed edge of each of said individual structures sealing said upper portion to said base portion of each of said individual hollow totally enclosed structures.]

[16. A process for controllably dispensing at a visibly detectable rate continuously or discontinuously for discrete periods of time a volatile composition of matter from a container into the atmosphere surrounding said container which process comprises the steps of:

(a) entrapping the volatile composition of matter in an entrapment agent whereby a temporarily entrapped volatile composition is formed;

(b) providing a first thin shell section composed of a thin polymer shell having a curved surface and having an inner void portion, an inner surface and an outer surface and having a first continuous sealable circumferential outer edge and a first geometric configuration;

(c) placing the entrapped volatile composition in the inner void portion of said first thin shell section and onto the inner surface of said first thin shell section, said volatile composition being selected from the group consisting of perfume compositions, herbicide compositions, insecticide compositions, animal repellant compositions, air freshener compositions, pheremone compositions, odor maskant compositions, deodorant compositions and insect repellent compositions;

(d) providing a second thin shell section having a second sealable circumferential edge and having a shape and volume which are such that when said second shell is placed in conforming adjacent edgewise contact with said first shell, a totally enclosed shell structure is produced with said entrapped volatile composition being totally enclosed within said shell section;

(e) placing said second thin shell section having said second sealable circumferential continuous edge which substantially conforms in shape to said first sealable circumferential edge onto said first thin shell section whereby said first sealable edge is in closely fitting sealable proximity with said second circumferential edge; and (f) sealing said first sealable edge to said second sealable edge whereby the resulting shell structure enclosing said entrapped volatile composition is totally enclosed and substantially air-tight with the exception of ingress and egress of volatile composition molecules controllably and at a constant velocity through the polymer wall during functional operation of the resulting shell structure;

at least a finite section of said first thin shell section or said second thin shell section comprising a microporous polymer having a porosity such that when said hollow totally enclosed structure thus formed is located in an inert gas at a pressure of less than or equal to about 1 atmosphere, said volatile material molecules are transported at a constant linear velocity and at a total derivative of concentration of volatile substance with respect to time onto the inner surface of said microporous polymer section via an adsorption mechanism and from the outer surface of said microporous polymer section via a desorption mechanism.]

[17. The process of claim 16 wherein the first thin shell section is composed of a non-porous and transparent polymer and said second thin shell section is a microporous polymeric membrane and is opaque at least at the instant in time of commencement of the functional operation of said structure, said microporous polymer membrane containing solid particles having an average particle diameter of from about 0.3 up to about 500 microns.]

[18. The process of claim 16 comprising the additional step (g) of placing the resulting shell structure when not in use into an outer all-enclosing container which outer container is non-porous and is composed of a material which prevents the volatile material molecules from being transported or diffusing therethrough, the dimensions of the outer container being such that the volume of said outer container and the shape of said outer container are such that the outer container totally encloses the inner container, said outer container having a sealable entrance therein whereby the shell structure defined according to claim 16 may be placed into and removed from said outer container and whereby said outer container may be sealed in an air-tight manner after the placing of said shell structure of claim 16 into said outer container.]

[19. The process of claim 16 wherein the volatile composition of matter entrapped in the entrapment agent is placed in a plurality of hollow totally enclosed structures which are laterally and detachably interconnected and which have a common midplane, each of said structures connected to at least one other of said structures (i) at a location midway between the base portion of each of said structures and the upper portion of each of said structures and (ii) along at least a portion of the circumferential sealed edge of each of said individual structures sealing said upper portion to said base portion of each of said individual hollow totally enclosed structures.]

[20. The hollow totally enclosed structure of claim 1 which is in the shape of a cylinder, the ends of the cylinder being microporous and the side of said cylinder being non-porous to said volatilizable composition of matter, at least a finite portion of the side of said cylinder being translucent.]

*21. A hollow totally enclosed structure comprising a thin shell totally enclosing an inner void, said thin shell having a base portion and an upper portion, said base portion having an inner surface:*

*(i) at least a finite portion of said thin shell being transparent whereby that portion of said inner void which is located proximate to the base portion of said totally enclosed structure is visible from without said thin shell, in the presence of visible wave-lengths of light;*

*(ii) contained totally within the said inner void of said thin shell and in place on said inner surface of said base portion, a volatile composition temporarily entrapped and totally entrapped at least at the instant in time of commencement of functional operation of said structure, in a gelatinous entrapment material, said volatile composition being selected from the group consisting of perfume compositions, herbicide compositions, insecticide compositions, animal repellent compositions, air freshener compositions, pheromone compositions, odor maskant compositions, deodorant compositions and insect repellent compositions, said gelatinous entrapment material containing said volatile composition having an upper surface;*

*(iii) at least a finite section of said upper portion of said thin shell comprising a microporous polymer and termed "a microporous polymer shell section" having a porosity such that when said hollow totally enclosed structure is located in an inert gas at a pressure of less than or equal to about 1 atmosphere, said volatile material molecule are transported at a constant linear velocity and at a constant total derivative of concentration of volatile substance with respect to time onto the inner surface of said microporous polymer section via an adsorption mechanism and from the outer surface of said microporous polymer section to the surrounding atmosphere via a desorption mechanism, said microporous polymer shell section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer shell section,*

*the volume of said gelatinous entrapment material being substantially less than the volume of said inner void, there existing at least one substantial void space between (i) said upper surface of said gelatinous entrapment material containing said volatile composition and (ii) said upper portion of said thin shell.*

*22. The hollow totally enclosed structure of claim 21 wherein the thickness of the microporous polymeric section is about 100 microns; the pore size is approximately 0.2 microns; the void volume of the microporous polymer section is approximately 34 cubic centimeters per gram and the density of the microporous polymer section is approximately 900 kilograms per cubic meter.*

*23. A structure comprising:*

*(a) a first hollow totally enclosed structure comprising a thin shell totally enclosing an inner void, said thin shell having a base portion and an upper portion, said base portion having an inner surface:*

*(i) at least a finite portion of said thin shell being transparent whereby that portion of said inner void which is located proximate to the base portion of said totally enclosed structure is visible from without said thin shell, in the presence of visible wave-lengths of light;*

*(ii) contained totally within the said inner void of said thin shell and in place on said inner surface of said base portion, a volatile composition temporarily entrapped and totally entrapped at least at the instant in time of commencement of functional operation of said structure, in a gelatinous entrapment material, said volatile composition being selected from the group consisting of perfume compositions, herbicide compositions, insecticide compositions, animal repellent compositions, air freshener compositions, pheromone compositions, odor maskant compositions, deodorant compositions and insect repellent compositions, said gelatinous entrapment material containing said volatile composition having an upper surface;*

*(iii) at least a finite section of said upper portion of said thin shell comprising a microporous polymer and termed "a microporous polymer shell section" having a porosity such that when said hollow totally enclosed structure is located in an inert gas at a pressure of less than or equal to about 1 atmosphere, said volatile material molecule are transported at a constant linear velocity and at a constant total derivative of concentration of volatile substance with respect to time onto the inner surface of said microporous polymer section via an adsorption mechanism and from the outer surface of said microporous polymer section to the surrounding atmosphere via a desorption mechanism, said microporous polymer shell section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer shell section and enclosing said first structure;*

*(b) a second air-tight totally enclosed structure, said first totally enclosed structure having a volume less than said second air-tight totally enclosed structure, said first totally enclosed structure being of such dimensions that it is (i) enclosable within said second air-tight totally enclosed hollow structure, and (ii) the internal volume of said second air-tight totally enclosed hollow structure is greater than the external volume of said first hollow totally enclosed structure,*

*the volume of the gelatinous entrapment agent being substantially less than the volume of said inner void, there existing at least one substantial void space between (i) said upper surface of said gelatinous entrapment material con-*

*taining said volatile composition and (ii) said upper portion of said thin shell.*

*24. A plurality of hollow totally enclosed structures laterally and detachably interconnected having a common midplane, each of said structures individually being a hollow totally enclosed structure comprising a thin shell totally enclosing an inner void, said thin shell having a base portion and an upper portion, said base portion having an inner surface:*

*(i) at least a finite portion of said thin shell being transparent whereby that portion of said inner void which is located proximate to the base portion of said totally enclosed structure is visible from without said thin shell, in the presence of visible wave-lengths of light;*

*(ii) contained totally within said inner void of said thin shell and in place on said inner surface of said base portion, a volatile composition temporarily entrapped and totally entrapped at least at the instant in time of commencement of functional operation of said structure, in a gelatinous entrapment material, said volatile composition being selected from the group consisting of perfume compositions, herbicide compositions, insecticide compositions, animal repellent compositions, air freshener compositions, pheromone compositions, odor maskant compositions, deodorant compositions and insect repellent compositions, said gelatinous entrapment material containing said volatile composition having an upper surface;*

*(iii) at least a finite section of said upper portion of said thin shell comprising a microporous polymer and termed "a microporous polymer shell section" having a porosity such that when said hollow totally enclosed structure is located in an inert gas at a pressure or less than or equal to about 1 atmosphere, said volatile material molecule are transported at a constant linear velocity and at a constant total derivative of concentration of volatile substance with respect to time onto the inner surface of said microporous polymer section via an adsorption mechanism and from the outer surface of said microporous polymer section to the surrounding atmosphere via a desorption mechanism, said microporous polymer shell section consisting essentially of a polyolefin intimately admixed with a powder having an average particle diameter of from about 0.3 up to about 500 microns, said powder being a filler material incompatible with said polymer, said powder being in a proportion of about 5 to 100 parts by weight per 100 parts by weight of polymer, the said volatile composition having a volatility at ambient conditions which is higher than the transmissibility of said microporous polymer shell section, each of said structures connected to at least one other of said structures (i) at a location midway between the base portion of each of said structures and the upper portion of each of said structures and (ii) along at least a portion of the circumferential sealed edge of each of said individual structures sealing said upper portion to said base portion of each of said individual hollow totally enclosed structures,*

*the volume of the gelatinous entrapment agent being substantially less than the volume of said inner void, there existing at least one substantial void space between (i) said upper surface of said gelatinous entrapment material containing said volatile composition and (ii) said upper portion of said thin shell.*

*25. A process for controllably dispensing continuously or discontinuously for discrete periods of time a volatile composition of matter from a container into the atmosphere surrounding said container, said container consisting of two oppositely coincidentally sealably fitting thin concave polymeric shells at least a finite portion of at least one of said shells comprising a microporous polymer wall section which process comprises the steps of:*

*(a) entrapping the volatile composition of matter in a gelatinous entrapment material whereby a temporarily entrapped volatile composition is formed;*

*(b) providing a first thin shell section composed of a thin polymer shell having a curved surface and having an inner void portion, an inner surface and an outer surface and having a first continuous sealable circumferential outer edge and a first geometric configuration;*

*(c) placing the entrapped volatile composition in the inner void portion of said first thin shell section and onto the inner surface of said first thin shell section, said volatile composition being selected from the group consisting of perfume compositions, herbicide compositions, insecticide compositions, animal repellent compositions, air freshener compositions, pheromone compositions, odor maskant compositions, deodorant compositions and insect repellent compositions, said gelatinous entrapment material containing said volatile composition having an upper surface;*

*(d) providing a second thin shell section having a second sealable circumferential edge and having a shape and volume which are such that when said second shell is placed in conforming adjacent edgewise contact with said first shell, a totally enclosed shell structure is produced with said entrapped volatile composition being totally enclosed within said shell section;*

*(e) placing said second thin shell section having said second sealable circumferential continuous edge which substantially conforms in shape to said first sealable circumferential edge onto said first thin shell section whereby said first sealable edge is in closely fitting sealable proximity with said second circumferential edge, whereby there exists at least one substantial void space between (i) said upper surface of said gelatinous entrapment material containing said volatile composition and (ii) said upper portion of said thin shell;*

*(f) sealing said first sealable edge to said second sealable edge whereby the resulting shell structure enclosing said entrapped volatile composition is totally enclosed and substantially air-tight with the exception of ingress and egress of volatile composition molecules controllably and at a constant velocity through said second thin shell section during functional operation of the resulting shell structure, at least a finite section of said second thin shell section being a microporous polymer section having a porosity such that when said hollow totally enclosed structure thus formed is located in an inert gas at a pressure of less than or equal to about 1 atmosphere, said volatile material molecules are transported at a constant linear velocity and at a total derivative of concentration of volatile substance with respect to time onto the inner surface of said microporous polymer section via an adsorption mechanism and from the outer surface of said microporous polymer section via a desorption mechanism, said microporous polymer section containing solid particles selected from the group consisting of talc and calcium carbonate having an average diameter of from about 0.3 up to about 500 microns, in a proportion of from about 5 to 100 parts by weight of polymer.*

* * * * *